(12) United States Patent
Pachl et al.

(10) Patent No.: US 7,488,602 B2
(45) Date of Patent: Feb. 10, 2009

(54) METHOD FOR DETECTING AND COMPENSATING AN UNDERDOSAGE OF TEST STRIPS

(75) Inventors: Rudolf Pachl, Ellerstadt (DE); Joachim Hoenes, Zwingenberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 747 days.

(21) Appl. No.: 10/686,970

(22) Filed: Oct. 16, 2003

(65) Prior Publication Data
US 2004/0136871 A1 Jul. 15, 2004

(30) Foreign Application Priority Data
Oct. 18, 2002 (DE) .............. 102 48 555

(51) Int. Cl.
- C12Q 1/32 (2006.01)
- C12M 1/34 (2006.01)
- A61B 5/00 (2006.01)
- G01N 21/77 (2006.01)

(52) U.S. Cl. .............. 436/169; 435/26; 436/514; 600/316

(58) Field of Classification Search .............. 436/169, 436/514; 435/26; 600/316
See application file for complete search history.

(56) References Cited

U.S. PATENT DOCUMENTS

| | | | | |
|---|---|---|---|---|
| 4,081,672 A | * | 3/1978 | Caspers et al. | 250/227.24 |
| 4,666,578 A | * | 5/1987 | Yamamoto | 204/549 |
| 5,114,350 A | | 5/1992 | Hewett | |
| 5,356,782 A | * | 10/1994 | Moorman et al. | 435/7.9 |
| 5,520,883 A | * | 5/1996 | Charlton et al. | 422/56 |
| 5,556,761 A | * | 9/1996 | Phillips | 435/14 |
| 5,723,308 A | * | 3/1998 | Mach et al. | 435/34 |
| 5,843,692 A | * | 12/1998 | Phillips et al. | 435/14 |
| 5,872,713 A | | 2/1999 | Douglas et al. | |
| 5,889,585 A | | 3/1999 | Markart | |
| 6,055,060 A | | 4/2000 | Bolduan et al. | |
| 6,064,896 A | * | 5/2000 | Rosenthal | 600/316 |
| 6,106,780 A | | 8/2000 | Douglas et al. | |
| 6,136,610 A | * | 10/2000 | Polito et al. | 436/514 |
| 6,140,137 A | * | 10/2000 | Sigler et al. | 436/536 |
| 6,268,167 B1 | * | 7/2001 | Wild et al. | 435/26 |
| 6,312,888 B1 | | 11/2001 | Wong et al. | |
| 6,362,890 B1 | * | 3/2002 | Petrich et al. | 356/432 |
| 6,365,417 B1 | * | 4/2002 | Fleming et al. | 436/514 |
| 6,541,266 B2 | * | 4/2003 | Modzelewski et al. | 436/95 |

(Continued)

FOREIGN PATENT DOCUMENTS

DE    30 29 301    2/1981

(Continued)

*Primary Examiner*—Jill Warden
*Assistant Examiner*—Lore Ramillano
(74) *Attorney, Agent, or Firm*—Barnes & Thornburg LLP

(57) ABSTRACT

The invention concerns a method for detecting an underdosage of an analytical test element and optionally for compensating the underdosage. The invention also concerns an analytical system and a test element which are suitable for detecting an underdosage.

Figure 1:
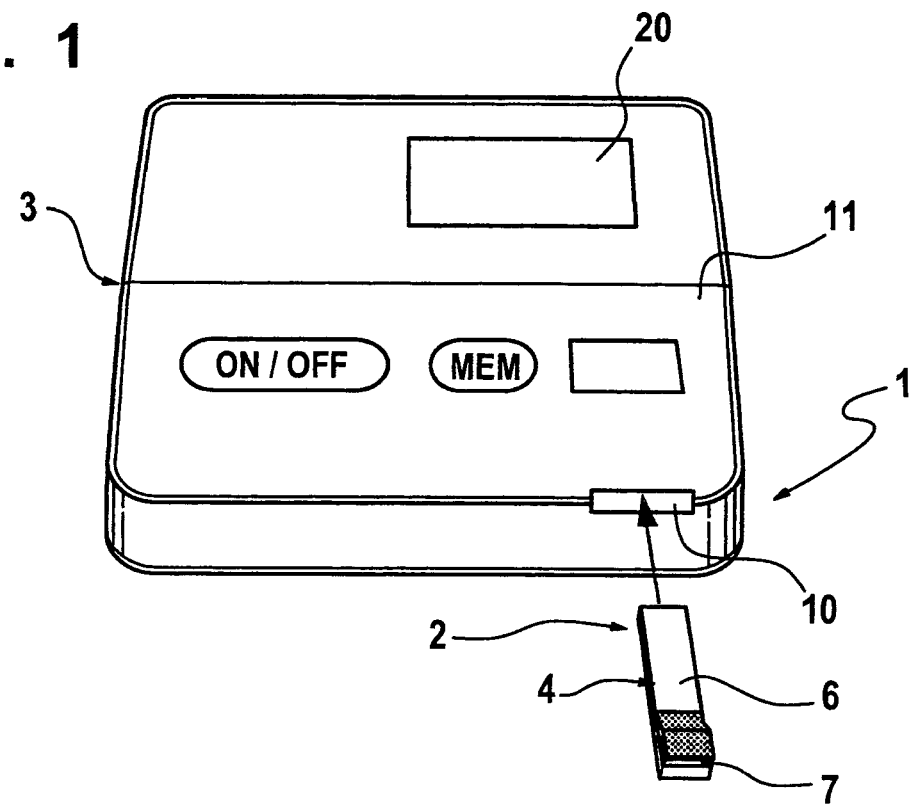

An underdosage of the test element can be reliably detected and optionally calculated by irradiating the analytical test element in a control wavelength range. For this purpose the test element contains a control substance which interacts with the radiation in the control wavelength range as a function of the contact with the applied amount of sample.

11 Claims, 3 Drawing Sheets

U.S. PATENT DOCUMENTS

| | | |
|---|---|---|
| 6,544,475 B1 | 4/2003 | Douglas et al. |
| 6,707,554 B1 | 3/2004 | Miltner et al. |
| 6,756,230 B2 | 6/2004 | Noda et al. |
| 2005/0227370 A1 * | 10/2005 | Ramel et al. ............... 436/514 |

FOREIGN PATENT DOCUMENTS

| | | |
|---|---|---|
| DE | 198 31 519 | 1/2000 |
| EP | 0 291 194 | 11/1988 |
| EP | 0 816 849 | 1/1998 |
| EP | 0 816 849 A2 | 1/1998 |
| EP | 1 111 386 A2 | 6/2001 |
| WO | WO 83/00931 | 3/1983 |
| WO | WO01/25171 A1 * | 4/2001 |

* cited by examiner

METHOD FOR DETECTING AND COMPENSATING AN UNDERDOSAGE OF TEST STRIPS

CROSS REFERENCE TO RELATED APPLICATION

The present application claims benefit of co-pending German Patent Application Serial No. 10248555.0, filed on Oct. 18, 2002, which is incorporated herein by reference.

The invention concerns a method for detecting an underdosage of an analytical test element and optionally for compensating the underdosage. The invention also concerns an analytical system and a test element which are suitable for detecting an underdosage.

Photometric evaluation of analytical test elements is one of the most common procedures in modern analytical methods for rapidly determining the concentration of analytes in samples. Photometric evaluations are in general used in the fields of analytics, environmental analysis and above all in the field of medical diagnostics. Test elements that can be evaluated photometrically play an important role especially in the field of blood glucose diagnostics from capillary blood.

There is a general trend in analytical testing towards reducing the amounts of sample. This is often due to the fact that only small amounts of sample are available. For example in the field of blood sugar determination, the diabetic takes a drop of blood from his finger pad. A reduction of the amount of blood required for a test can make blood sample collection less painful for the person to be examined. This is mainly due to the fact that the depth of the incision for blood collection can be selected to be less deep when a small sample volume is required than when a larger volume of sample is required.

A reduction of the amounts of sample is associated with a miniaturization of the test elements and in particular the detection zones in which the reaction of the sample containing the analytes occurs. However, it has turned out that it is not feasible to miniaturize the detection zones of test elements that are to be evaluated photometrically to any desired degree since the size of the area that is to be examined photometrically is of major importance for a reliable determination of the analyte concentration. Furthermore it is important that the area of the detection zone that is examined photometrically should be wetted by the sample as completely and homogeneously as possible. However, it is not always possible to ensure this from the beginning especially with small sample volumes. Hence it is important to detect whether sufficient sample material is in fact present for the respective measurement and/or whether the sample material has led to a homogeneous colouration over the entire area of the detection zone.

In the current commercial photometric blood sugar test systems designed for home monitoring which usually consist of a reflection photometer and suitable blood sugar test elements (test strips) an underdosage of the detection zone of the test strip that may have occurred is detected either visually by the user (as is for example the case with the products "Glucotouchg" from Lifescan Inc. or "Accutrend®" from Roche Diagnostics GmbH) or by comparing the reflectance values that have been obtained by measuring the reflectance of two or more zones of the detection zone (light spots) that are in close proximity or partially overlapping (cf e.g. EP-A 0 819 943 and the product "Glucotrend®" from Roche Diagnostics GmbH).

In the method of visual control by the user it is his duty to decide whether the criteria for an adequate wetting of the detection field are met or not. This may result in faulty measurements when the test strips are underdosed especially in the case of visually handicapped persons. When the volumes required are relatively small and hence the areas are small, visual examination of the applied amount of sample reaches its limits even for persons with normal vision.

A very reliable detection of underdosage can be achieved by the method of comparing two or more adjacent or partially overlapping light spots. However, the detected underdosage always has the effect that the measuring instrument gives no result for the measurement in the case of underdosed test elements. Furthermore two or more adjacent light spots compared to one light spot inevitably lead to an enlargement of the area that has to be covered by the sample liquid and hence to an increase in the required sample volume.

The document U.S. Pat. No. 5,114,350 proposes that the increase in transparency and thus the decrease in the reflectance of the detection zone caused by wetting with the sample liquid should be determined in order to detect and monitor the degree of wetting of the detection zone of a test element. For this the dry, unwetted detection zone is firstly illuminated and the reflectance is determined using an apparatus. The wetting of the test element leads to a decrease in the reflectance and in the measured reflectance value until the reflectance value reaches a plateau when the test element is completely wetted. When the reflectance plateau is detected by a control unit, application of the sample to the test element is discontinued. After detection of the amount of sample, the same optical system is used to measure a reflectance value of the test element resulting from an analyte-dependent colour formation. The analyte-dependent change in reflectance also reaches a plateau value when the reaction of an analyte with a colour-forming reagent is completed.

The analyte concentration is calculated from the analyte-dependent reflectance value (plateau value) taking into account the plateau value that is measured when the test element is completely wetted. Hence the analyte concentration is calculated with reference to the applied sample volume. If a complete wetting has not occurred, the degree by which the reflectance is decreased allows detection of an underdosage of the detection element and determination of the actual amount of sample present.

An optical arrangement is used to measure the change in reflectance caused by the wetting of the detection zone of the test element and to measure the analyte-dependent change in reflectance which has the same source of radiation, optical path and detector for the respective measurements. Consequently the analyte concentration can only be determined by means of a plurality of successive measurements in order to allow determination of the respective plateau value.

Another requirement is that the system must be designed such that an interruption of the sample supply is ensured when the first plateau value is reached.

Consequently the measurement procedure and the construction of the device turn out to be time consuming and complicated.

A method for detecting adequate wetting of an analytical test element with aqueous sample liquid is also known from the document WO-A 83/00931. In addition to detecting a possible underdosage, the method can also be used to estimate the sample volume that has been actually applied to the test element. The method utilizes the optical absorption properties of water in the sample liquid especially in the infrared spectral range and hence its application is limited to aqueous sample liquids. Moreover an infrared optical system is necessary due to the absorption bands of water which often turns out to have a complicated construction.

The object of the present invention is to eliminate the disadvantages of the prior art. In particular the object of the invention is to provide a method and a system that detect an erroneous dosing with a high degree of precision without requiring a complicated optical system or method.

This object is achieved by the subject matter of the invention as characterized in the independent patent claims. Preferred embodiments of the invention are stated in the dependent claims.

The invention concerns an analytical system for determining the amount of sample in an evaluation area of a test element. The analytical system comprises an illumination unit which emits radiation in a control wavelength range in which a control substance interacts with the radiation in a manner which depends on contact with a sample matrix. The system also comprises a detector for detecting the radiation that has interacted with the control substance to generate a detection value.

An amount of sample in an evaluation area of a test field can be determined by means of an evaluation unit. For this the detected radiation is compared with a known detection value for the control substance for a known amount of sample in the evaluation area and used to determined the amount of sample.

Another subject matter of the invention is a test element for detecting an amount of sample. The test element comprises a test field containing a reagent which interacts with an analyte of a sample in such a manner that the analyte-specific reagent interacts with the radiation as a function of the analyte concentration when the test field is irradiated in a detection wavelength range. In order to detect an amount of sample applied to the test element, the test element also contains a control substance in the test field that interacts with a sample matrix of the sample such that the control substance interacts with the radiation as a function of the amount of sample applied to the test field when the test field is irradiated in a control wavelength range.

The system or method according to the invention enables a reliable detection of incorrect dosage on a test element. In this connection the actual amount of applied sample or the degree of coverage of the test element is advantageously determined so that a correction can be calculated in the case of an incorrect dosage and the user is not forced to apply another sample of blood. However, if the degree of coverage is below a predetermined threshold, the evaluation of the measured value is discontinued in another preferred embodiment since the accuracy of the measured value cannot be guaranteed despite the correction calculation.

Suitable selection of the control substance allows a free selection of the control wavelength range so that it is for example not necessary to measure in the IR range. Hence the design of the instrument optics can be kept cheap. Furthermore interfering overlapping water bands in the IR range can be avoided.

The term control substance encompasses substances that interact with the sample matrix on contact. In this connection the contact of the control substance with the sample matrix occurs in such a manner that a detection value is detected when the control substance is irradiated in the control wavelength range which changes as a function of the amount of sample. For example a change in the detection value can be caused by a change in the physical and/or chemical properties of the control substance when it comes into contact with the sample matrix.

In this connection a detection value is understood as a value that is generated after irradiation of the test element e.g. by radiation that is reflected, transmitted or emitted from the test element.

If the radiation is reflected or transmitted from the test element, a change in the detection value may for example be caused by a change in the absorption properties of the control substance. In this connection it is for example conceivable that the control substance forms a dye that absorbs in the control wavelength range when it comes into contact with the sample matrix. The detection value is then generated by the radiation reflected or transmitted by the test element as a function of the dye that is formed. It is also conceivable that the control substance for example comprises a luminescent substance such that luminescence is excited by irradiation in the control wavelength range when the control substance comes into contact with the sample matrix in which case the intensity of the luminescence is determined by the amount of applied sample.

The term contact or interaction with the sample matrix means within the scope of the invention any possible form of interaction of the control substance with the sample matrix. If the control substance is a colour former, a coloured substance may form as a result of a chemical reaction or van der Waals' interactions. The absorption of the coloured substance that is formed is then measured in an evaluation area of the test field and is a measure of the amount of applied sample. If the control substance is a luminescent substance, all possible interactions with the sample matrix are also conceivable which impair or enable luminescence. In this case it is for example possible to use a luminescent substance as the control substance whose luminescence properties change on contact with the sample matrix (e.g. by quenching the luminescence). It is also possible to use substances which are not able to luminesce until contact with the sample matrix. Hence as already described the term contact with the sample matrix also, among others, encompasses luminescence being only impaired by impact between sample matrix molecules and molecules of the control substance. The interaction of the control substance with radiation in the control wavelength range can consequently be directly (e.g. by forming a dye or a luminescent substance) or indirectly (e.g. change in the intensity of luminescence by quenching processes) dependent on the contact with the sample matrix.

In principle the method is neither limited to a particular interaction of the control substance with the sample matrix nor to processes which influence the interaction of the control substance with electromagnetic radiation as a function of the amount of sample provided the contact with the sample matrix causes a measurable change in the interaction of the control substance with radiation and the amount of applied sample can be inferred from this measurable change.

The term amount of sample can for example be understood within the scope of the invention as information on the absolute volume or amount of applied sample.

However, an absolute amount of sample is often not determined but rather advantageously a degree of coverage of the test field which allows conclusions to be drawn about an adequate sample application. In general there are a diversity of possible measures for the amount of sample which allow conclusions to be drawn about the amount of sample that interacts with the analyte-specific reagent. For example methods for analyte determination are described in the prior art by which the amount of sample that comes into contact with an analyte-specific reagent can be inferred from the degree of coverage of the test field. Such methods and systems are for example disclosed in EP 0 819 943.

Due to the precise determination of the amount of sample on a test element, the method and system according to the invention are advantageously used to determine an analyte concentration. In this connection the invention has proven to be particularly suitable for modern analytical methods in particular in the home monitoring field. In this field of application particularly high demands are made on an analytical system since an important aim, especially in the home monitoring field, is to precisely determine an analyte concentration despite a reduction of the amount of sample without requiring complicated apparatus. However, since especially home monitoring instruments are demonstrably often used by untrained and elderly users, erroneous dosing of the sample on a test element often occurs. The system according to the invention allows a simple instrument design so that the manufacturing costs for the analytical systems remain low and affordable as a home monitoring system for patients. The patients do not have to carry out a complicated blood withdrawal for the system/method according to the invention since it is possible to minimize the amount of sample required for the analysis. This takes into consideration that an erroneous dosage is very serious especially for concentration determinations from small amounts of sample since even small variations in the amount of sample can result in considerable errors in the concentration calculation.

Such faulty dosing is detected in an advantageous embodiment of the system according to the invention by comparing the detected radiation with a known detection value of the control substance for a known amount of sample in the evaluation area. The comparison with the known detection value can be preferably carried out by only registering whether it is above or below the known absorption value without a more detailed quantification of the amount of sample.

However, with the inventive solution an underdosage of the evaluation area of a test element can advantageously not only be reliably detected but also compensated —advantageously up to a certain threshold value. Hence in the case of a faulty dosage the user does not have to withdraw blood again.

An underdosage in the sense of the invention is when a region on the surface of the test element (evaluation area) is not completely covered with sample liquid. In this case an area that is to be evaluated by reflection photometry is not completely available for the analyte detection reaction but only a fraction thereof. The absorption of the analyte detection reaction is then erroneously related to an amount of sample that is too large and hence a concentration that is too low is given as the measured value. The system according to the invention corrects the measured value taking into consideration the actual amount of sample applied.

The term "evaluation area" in this context encompasses the area of the test field which is irradiated by the illumination unit and can for example be the same as the test field in which case a complete irradiation of the test field takes place.

In addition to detecting and compensating an actual underdosage, inhomogeneities in the sample distribution in the detection element which are not due to an inadequate amount of sample liquid are also taken into account. Such inhomogeneities in the detection element may for example be due to the manufacturing process.

Within the scope of the invention the term sample means in particular body fluids such as blood, saliva, urine or liquids derived from body fluids such as serum, plasma, diluted blood, saliva or urine samples.

An analyte is determined from a sample for example by using a test element as is well known in the prior art e.g. for glucose determination from blood U.S. Pat. No. 6,036,919 or for enzyme determination from plasma DE 3130749. In this case the analyte reacts with a reagent present in the test element and forms a dye depending on the analyte concentration. The analyte concentration is determined on the basis of the measured absorption of the dye. The absorption is for example measured by reflection photometry, but it is also possible to measure transmission or fluorescence. In general the system and method according to the invention are not limited to reflectance measurements but encompass other variants.

In an advantageous embodiment the reflectance amplitude that is available for measuring the analyte is selected to be as large as possible. This maximizes the range of reflectance values between minimal and maximal analyte concentrations since the reflectance amplitude has a large influence on the precision of the reflection photometric measurements. The reflectance amplitude is proportional to the area of the detection element that is covered with sample liquid. If a colour former is used as a control substance, it has proven to be advantageous to select the colour of the chromophore whose formation depends on the degree of coverage in such a manner that at a selected wavelength (control wavelength range) a very low and preferably no reflectance is observed when the examined evaluation area is completely wetted in order to achieve a large difference in the reflectance values and thus a precise determination of the area of the detection element that is actually moistened. The reflectance obtained in the presence of the sample should be particularly preferably as high as possible.

In practice it is advisable to set a lower threshold value for the area of the detection element that is covered with sample liquid. In an advantageous embodiment the value of the determined amount of sample is compared with a previously stored threshold value. For values above this threshold the precision of a measurement meets the quality requirements of the measuring system and hence the output of a measured value should be suppressed for values below this threshold value.

The relationship between the reflectance that is found and the actual wetted area can be stored in a known manner in the measuring instrument or can be transferred to the measuring instrument together with other lot-specific data for the test elements for example by means of a barcode, ROM key or an input keyboard.

Fluorescein can for example be used as a control substance in the sense of the invention.

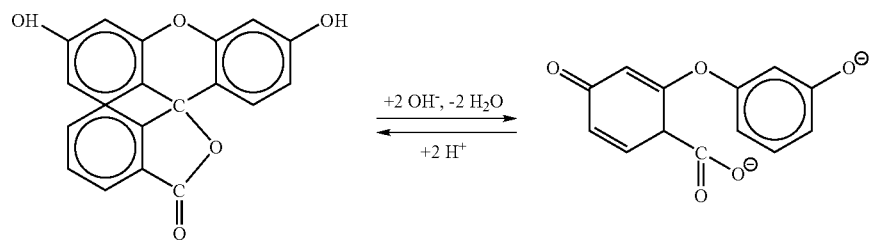

On contact with the sample matrix, fluorescein is hydrolysed by water present in the sample matrix. If fluorescein is subsequently excited to fluoresce there is an increased intensity of the fluorescence as a function of the wetting of the test field.

Furthermore a colour former can be used as the control substance in the sense of the invention which indicates the presence of the sample in the test element by a colour change that can be easily observed. A large number of substances are known which change their colour due to the presence of samples. In this connection the manner in which the sample interacts with the substance that can change its colour is less important for the present invention. It is important that the extent of the colour change correlates with the amount of sample or the degree of coverage of the evaluation area. In this connection the amount of sample which comes into contact with the control substance should advantageously enable an inference of the amount of sample which interacts with the reagent.

The control substance advantageously does not interact with radiation in the control wavelength range when no reagent. Multilayered test elements are described for example in the documents U.S. Pat. No. 6,036,919 and U.S. Pat. No. 5,846,837. An example of an analyte-specific reagent is 2,18-phosphomolybdic acid ($P_2Mo_{18}O_x$) which is used to determine the glucose concentration.

The glucose present in the sample reacts with the reagent to form a dye. The absorption of the analyte-dependent dye is firstly measured by the analytical system in a first wavelength range which in the case of 2,18 phosphomolybdic acid is at 660 nm to allow the determination of the glucose concentration. Afterwards or before detecting the analyte-dependent dye, a measurement is carried out in the control wavelength range so that for example the absorption of an analyte-independent dye is detected. In a preferred embodiment of the test element for determining the amount of sample, a test field contains chlorophenol red as an analyte-independent colour former. After applying the sample, e.g. blood, to the test field, the ring of the sulfonic acid group of chlorophenol red is opened by the water present in whole blood and a dye having an absorption maximum at 572 nm is formed.

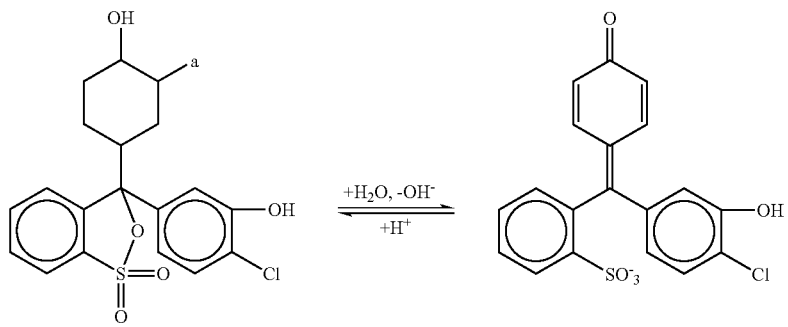

sample has been applied to the test field. After sample application the control substance advantageously continues to not interact in the detection wavelength range. If a chromophore is used as a control substance, the control wavelength range is preferably between 500 and 600 nm, more preferably at 572 nm.

Within the scope of the invention a sample matrix means all sample components which are not referred to as analyte and are present in adequate amounts in the sample. For example for biological liquids the term sample matrix can encompass water such that the water present in the sample matrix forms a dye with the colour former in the test field.

In this case a colour change means that the chemical compound changes its colour in the presence of sample liquid (colour change), is converted from a colourless into a coloured state (formation of colour) or conversely, changes from a coloured to a colourless state (disappearance of colour).

The chemical compound is preferably converted in the presence of sample liquid from a colourless into a coloured state. Ideally the measured reflectance at the wavelength of the chromophore formed in this manner is inversely proportional to the area of the detection element of the test strip that is actually wetted with sample liquid.

In this case a test element is for example used which consists of two layers. The layered structure ensures that the detected sample quantity or the degree of coverage of the test field allows conclusions to be made about the amount of sample which comes into contact with the analyte-specific After detecting the absorption of chlorophenol red at 572 nm, the measured absorption value is compared with an absorption value for chlorophenol red for a predefined known amount of sample. The amount of blood sample can be inferred by comparing the absorption values of chlorophenol red with one another. The calculated amount of sample is subsequently taken into consideration for the glucose determination in order to exactly determine the measured glucose concentration taking into consideration the applied amount of sample. Consequently an advantageous analytical system for this purpose comprises an illumination unit that can emit radiation in at least two different wavelength ranges.

Hence the measurement for determining the amount of sample advantageously takes place in a wavelength range which is different from that of the analyte determination. This allows a maximum reflectance amplitude for the sample quantity as well as for the analyte determination among others which optimizes the accuracy of the method.

Furthermore a method for determining an amount of sample in an evaluation area of a test element is a subject matter of the invention.

The method comprises irradiating a sample on a test field of a test element. In this process the test field is irradiated in a control wavelength range in such a manner that at least one evaluation area of the test field is contacted by the radiation. The test field of the test element contains a control substance which interacts with a sample matrix of the sample in such a manner that the control substance interacts with the electromagnetic radiation in the control wavelength range as a function of the contact with the sample matrix. Radiation which has interacted with the control substance is detected to generate a detection value. The amount of sample in the evaluation area is determined by comparing the detected radiation with a known detection value of the control substance for a known amount of sample in the evaluation area.

Advantageous embodiments of the method are derived as already described. Preferred embodiments of the system and the test element are suitable for carrying out the method.

The invention is further elucidated by the figures and the following examples:

If a colour former is used as the control substance, the preferred case is always described in the following for the sake of simplicity and clarity i.e. that in which the chemical compound that serves as an indicator and measure for the presence of sample liquid in the evaluation area changes from a colourless state without sample contact to a coloured state with sample contact. Of course the invention is not limited to this case. By considering analogies the invention can easily be applied to the cases of "colour change" and "disappearance of colour". These cases are explicitly encompassed.

FIG. 1: analytical system with test element

Figure 2:
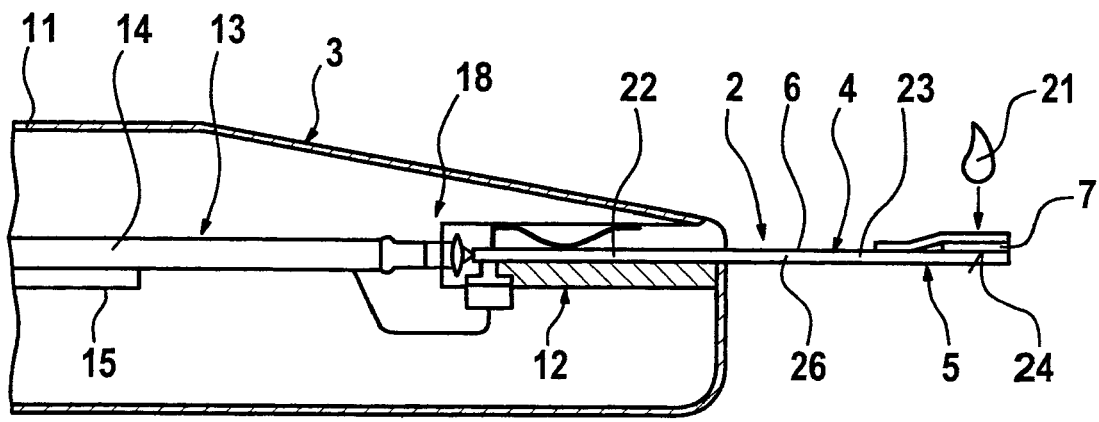

FIG. 2: analytical system with light-conducting test element

Figure 3:
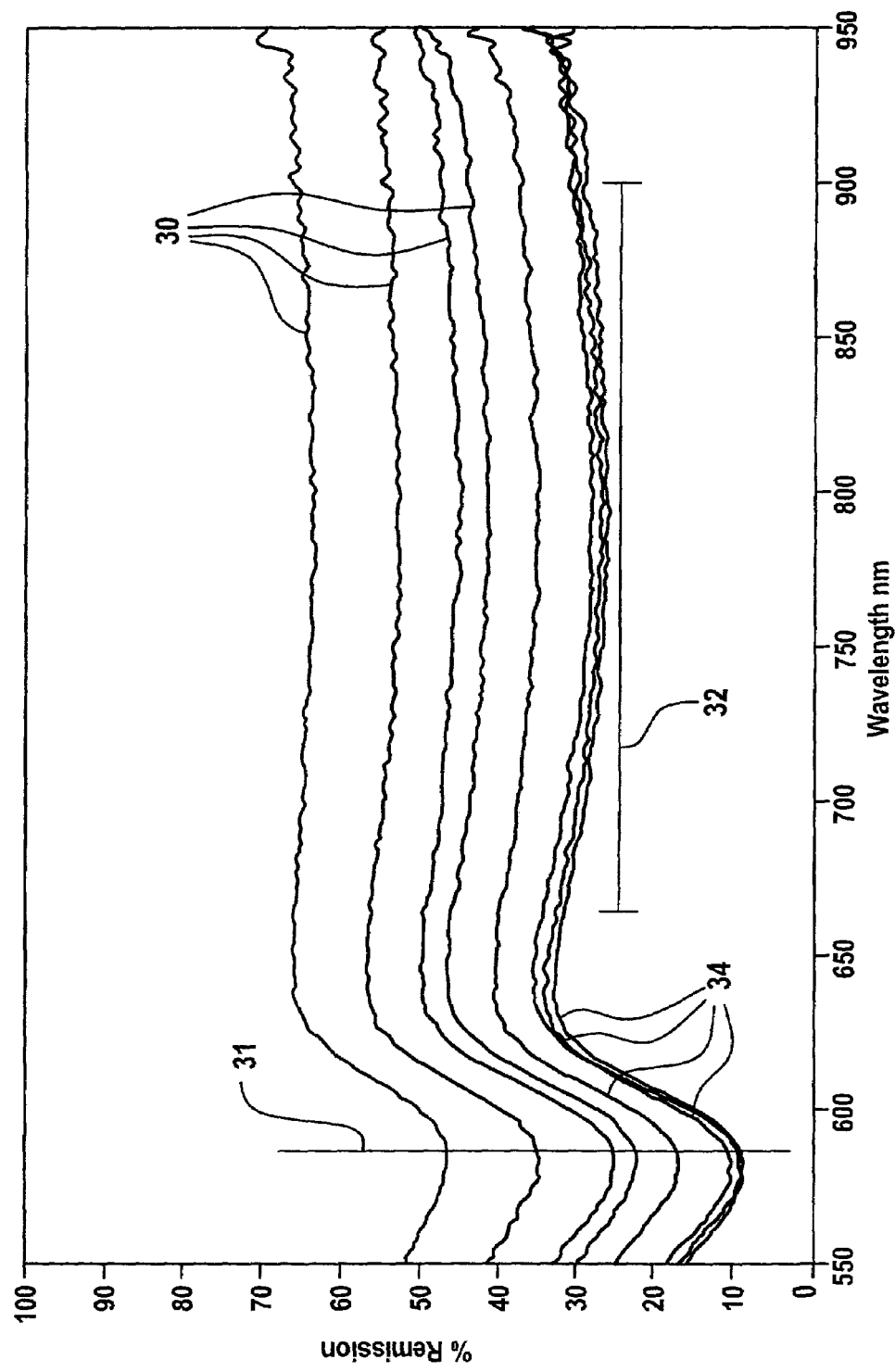
Figure 4:
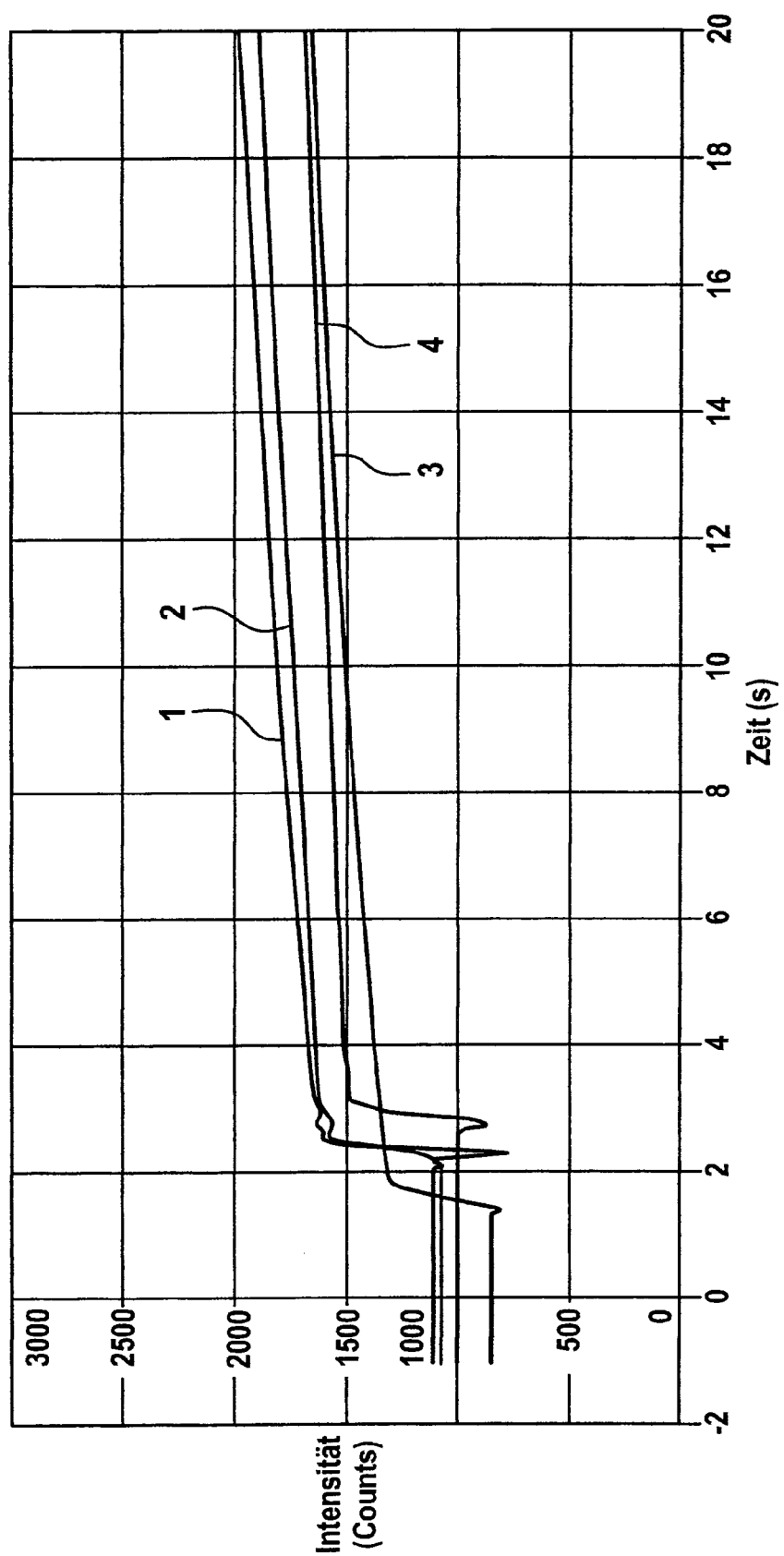

FIG. 3: absorption bands of chlorophenol red in the range from 550 to 950 nm FIG. 4: fluorescence measurements of fluorescein at 420 nm The analytical system (1) shown in FIG. 1 comprises a test element (2) and an evaluation instrument (3). The test element (2) consists of a test strip (4) having an elongate support foil (5) made of plastic and a test field (7) attached to the upper flat side (6) of the support foil (5).

The test element (2) is inserted through an opening (10) in the housing (11) of the evaluation instrument (3) into a test element holder (not shown) and positioned in a measuring position. The evaluation instrument (3) comprises measuring and evaluation electronics (13) consisting of a printed circuit board (14) and integrated circuits (15). A light emitter preferably in the form of a light emitting diode (LED) and a detector preferably in the form of a photodiode which are components of an optical measuring device (not shown) are connected to the measuring and evaluation electronics (13).

FIG. 2 shows details of the application of the method according to the invention in an analytical system with light conducting test elements which are for example described in the prior art (WO 01/48461). In this case the application of the method and system according to the invention proves to be particularly advantageous since conventional methods of the prior art can often not be used to detect underdosages in such systems.

In order to carry out an analysis, a drop of sample liquid (21) is applied to the side (upper side) of the test field (7) that faces away from the support foil (5). Sample application is facilitated by the fact that only a first section (22) of the test element (2) positioned in the measuring position is inside the housing (11) whereas a second section (23) containing the test field (7) juts out from the housing (11) and is thus readily accessible. The liquid penetrates and dissolves the reagents present in the test field (7). The reaction of the analyte present in the sample with the reagent system results in an optically measurable change and in particular a colour change. For the photometric evaluation an evaluation area (24) of the test field (7) is illuminated with primary light of a first wavelength and the diffusely reflected secondary light intensity is measured. In the light-conducting test element that is shown this occurs by means of a special design of the test strip (2) and the interacting parts of the optical measuring device (18).

The support foil (5) comprises at least one optical light-conducting layer (26). More detailed information on light-conducting elements whose light transport is based on total reflection can be found in the relevant literature.

In the example shown the test strip (2) is used to determine the glucose concentration and for this purpose the test field contains the reagent 2,18 phospho-molybdic acid. The reagent reacts with the glucose and forms a coloured complex which absorbs at ca. 660 nm. Reagents that can be used to detect a glucose concentration on test carriers are well-known in the prior art and are described for example in the document U.S. Pat. No. 6,036,919. Of course any other form of a reagent system is in principle conceivable in which the detection wavelength range advantageously differs from the control wavelength ranges. Furthermore it is also possible to directly detect the analyte that is to be determined in the detection wavelength range without prior interaction with a reagent.

The test element (2) also contains a colour former which is also present in the test field (7). As a result of the water that is present in the sample, the colour former reacts after sample application (21) to form the dye chlorophenol red.

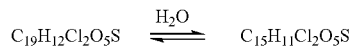

If the test strip (2) is now evaluated with the aid of an analytical instrument (1), radiation is firstly emitted in the detection wavelength range of 660 nm so that the radiation reflected by the test field (7) is detected as a function of the glucose concentration present in the sample. The detected signal intensity firstly corresponds to the absolute amount of glucose that is present in the measured sample. Subsequently the test field is irradiated in a control wavelength range of ca. 572 nm. Chlorophenol red absorbs in this wavelength range in the presence of water so that almost no reflectance is detected as soon as the test field (7) is completely covered with the sample (21).

Since in the example shown the sample (21) is a drop of blood, it can be assumed that sufficient water is present in the sample to completely convert the colour former as soon as it comes into contact with the sample. In principle a large variety of constituents of the sample matrix can be envisaged which interact with the colour former and form a dye. In this connection one only has to take care that the interacting substance in the sample matrix is present in a sufficient quantity to result in a predetermined absorption of the dye as a function of the amount of sample as soon as the test field comes into contact with the sample.

In contrast to the prior art in which for example water is directly detected, the use of the control substance according to the invention enables a free choice of the control wavelength range and provides a discrete absorption band. Interfering absorption bands e.g. of pure water which would otherwise lead to overlapping can be avoided by suitable selection of the wavelength range.

The detected signal of the dye in the control wavelength range is recorded and compared with an absorption value (calibration value) of the dye when for example the test field is completely covered by the sample. Comparison of the measured absorption value with the calibration value enables the volume of the sample to be calculated or to be directly determined. Afterwards the previously determined amount of glucose is related to the amount of sample to yield an exact determination of the glucose concentration. This is communicated to the user by means of the display (20). If the sample has been underdosed to such an extent that the quality of the measurement can no longer be guaranteed, the applied amount of sample falls below a stored threshold value. If the system finds that the value is below the threshold, the output of a measured result is refused and the user is informed about the invalid measurement by means of the display and prompted to repeat the measurement.

FIG. 3 shows various absorption bands (30 and 34) of chlorophenol red that are detected when measuring different sample volumes on the test field. In FIG. 3 the wavelength range in nm is plotted versus the reflectance starting at 100% reflectance when there is no absorption by the test element and no sample is applied to the test element.

The absorption maximum (31) of chlorophenol red is at 572 nm as already described. If sufficient sample is applied to the test element so that the test field is completely covered, the dye absorbs the light such that a reflectance minimum of the light in the range of 9-13% is detected by the detector. If a reflectance in this range is measured i.e. an almost complete absorption of the light has occurred, sufficient sample has been applied to the test element. However, if the light intensity exceeds a predetermined reflectance value (e.g. 15%), insufficient sample has been applied to the test strip and hence the test strip is underdosed. However, the reflectance value above which the test element is regarded as underdosed changes depending on the analytical system. An underdosage of the test element is for example advantageously already detected at 3% reflectance. Then the measured reflectance must be used as a basis to infer the applied amount of sample or the degree of coverage of the test field before a glucose concentration can be calculated. The detection value recorded for a complete coverage of the test field can be used to infer the degree of coverage of the test field for the measured reflectance value.

It turns out that there is a linear relationship between the measured reflectance and the degree of coverage of the test field or the applied amount of sample.

The absorption of the analyte-specific reagent is then measured in a second measurement in the range (32) of 650 and 900 nm. The light is absorbed by varying degrees depending on the absolute amount of glucose present in the sample. FIG. 3 illustrates the increase in the reflectance as the absolute amount of glucose decreases. The decrease in the absolute amount of glucose is achieved in the example shown by reducing the amount of sample and consequently by an inadequate coverage of the test field while the glucose concentration in the respective samples is identical.

If for example the reflectance is measured at 750 nm to determine the glucose concentration, a reflectance value of 75% is used to determine the glucose concentration when there is an adequate amount of sample. However, if the same sample is measured on an underdosed test field, this would result in a reflectance between 85% and 90% and thus falsely infer a glucose concentration that is too low. Consequently the glucose concentration must be determined taking into consideration the measured absolute amount of glucose and the determined degree of coverage of the test field.

However, if the light intensity in the control wavelength range exceeds a threshold value (35), the determination of the glucose concentration would prove to be unreliable and not sufficiently accurate despite a correction of the measured glucose value by the determined degree of coverage. This for example applies to an underdosage where less than ⅓ of the test field is covered. The glucose concentration would no longer be displayed to the user when the corresponding reflectance value is exceeded and instead the user would be prompted to repeat the sample application.

FIG. 4 illustrates an analogous method according to the invention for detecting an underdosage which is based on a detection of fluorescence. Preferred embodiments are derived as already described so that in this case threshold values can also be determined and when the value falls above or below the threshold value the measured value has to be corrected or output of a measured value is refused. Such methods that are based on fluorescence measurements are for example used to determine glucose in blood.

In the example shown the test field of a test element is prepared with the fluorophore fluorescein as a control substance. The test field contains the substance $NAD^+$ as the analyte-specific reagent for detecting glucose. When a blood sample is applied to the test field, the fluorophore reacts with the water present in the sample resulting in hydrolysis of the fluorescein as the control substance.

FIG. 4 shows the time course of the fluorescence intensity after applying a blood sample to the test field and after irradiating the test field at an excitation wavelength. After contact with the sample matrix the intensity of the fluorescence of fluorescein changes due to the hydrolysis. If the test field is irradiated at 485 nm only the hydrolysed fluorescein is excited such that after about 1 second fluorescence radiation is emitted from the test field in the range >570 nm. Advantageously the intensity of the fluorescence is measured about 4 seconds after irradiating the test field. It has turned out that the intensity of the fluorescence radiation depends on the applied amount of sample since only the portion of the control substance is excited which has come into contact with the sample matrix. If too little sample has been applied to the test field, the fluorescein is not completely hydrolysed resulting in a reduced intensity of fluorescence. There is a linear relationship between the wetting of the test field with the sample and the fluorescence intensity. If the amounts of applied sample differ only slightly as shown by the curves 1 and 2 of FIG. 4 this results in corresponding slight differences in the fluorescence intensity. If the applied amount of sample is reduced further (see curves 3 and 4) this results in a corresponding reduction of the fluorescence intensity.

If the time course of the emission of fluorescence after irradiating the sample on the test field is known, the measuring conditions can be correspondingly predefined such that the applied amount of sample can be deduced from the intensity of the fluorescence. This can for example be accomplished when the time of measurement is always 4 seconds after exciting the control substance. The measured fluorescence intensity can then be used to deduce the amount of sample on the basis of the fluorescence intensity measured for a known amount of sample.

The invention claimed is:

1. A method of operating an analyte evaluation instrument to determine the analyte content of a sample disposed on a test element, the method comprising:
    operating an optical measuring device to determine the amount of the sample placed on the test element based on an interaction between a control substance disposed on the test element and a sample matrix of the sample;
    operating the optical measuring device to determine the analyte content of the sample based on an interaction between a reagent disposed on the test element and the analyte in the sample; and
    correcting the analyte content of the sample if the amount of the sample placed on the test element is determined to be less than a predetermined calibration value.

2. The method of claim 1, wherein:
    determining the analyte content of the sample includes determining the glucose content of the sample.

3. The method of claim 1 wherein the interaction between the control substance and the sample matrix is a chemical reaction.

4. A system for detecting an underdosage of a test element, the system comprising:
    an optical measuring device that includes (i) a light emitter device capable of illuminating the test element with (A) light capable of generating a first photometrically detectable signal upon interacting with a reagent disposed on the test element after the reagent interacts with an analyte contained in a sample disposed on the test element and (B) light capable of generating a second photometrically detectable signal upon interacting with a control substance disposed on the test element after the control substance interacts with a sample matrix of the sample disposed on the test element and (ii) a light detector device capable of receiving the first photometrically detectable signal and the second photometrically detectable signal;

an electronic circuit operatively coupled to the optical measuring device, wherein the electronic circuit is configured to:

analyze the first photometrically detectable signal from the optical measuring device to determine the analyte content of the sample based on the concentration of the analyte in the sample, and analyze the second photometrically detectable signal from the optical measuring device to determine whether an underdosage of the sample has occurred on the test element based on the interaction between the control substance and the sample matrix.

5. The system of claim 4 wherein:

the electronic circuit is further configured to correct the analyte content of the sample if the amount of the sample placed on the test element is determined to be less than a predetermined calibration value.

6. The system of claim 4 wherein the sample is blood, the analyte is glucose, and the electronic circuit is configured to:

analyze the first photometrically detectable signal from the optical measuring device to determine the glucose content of the sample, and analyze the second photometrically detectable signal from the optical measuring device to determine whether an underdosage of blood has occurred on the test element.

7. An analyte evaluation instrument, comprising:

an optical measuring device, and an electronic assembly electrically coupled to the optical measuring device, the electronic assembly being operable to:

operate the optical measuring device to assess the volume of a liquid sample placed on a test element, the assessment being based on an interaction between a control substance disposed on the test element and a sample matrix of the liquid sample, and operate the optical measuring device to determine the analyte content of the liquid sample based on the concentration of the analyte in the liquid sample.

8. An analyte evaluation instrument, comprising:

an optical measuring device, and an electronic assembly electrically coupled to the optical measuring device, the electronic assembly being operable to:

analyze output from the optical measuring device so as to assess the amount of sample placed on a test element, wherein the assessment is based on an interaction between a control substance disposed on the test element and a sample matrix of the sample, analyze output from the optical measuring device to determine the analyte content of the sample, wherein the determination is based on an interaction between a reagent disposed on the test element and the analyte in the sample; and the electronic assembly is further operable to correct the analyte content of the sample if the amount of the sample placed on the test element is determined to be less than a predetermined calibration value.

9. A system for evaluating the concentration of an analyte in a sample, comprising:

a test element having (i) a test field for accepting the sample, (ii) a reagent in the test field, the reagent being capable of interacting with the analyte in the sample, wherein the interaction between the reagent and the analyte causes a first photometrically detectable signal to be produced when the test field is illuminated with light, and (iii) a control substance in the test field, the control substance being capable of interacting with a sample matrix of the sample, wherein (A) the interaction between the control substance and the sample matrix causes a second photometrically detectable signal to be produced when the test field is illuminated with light and (B) the second photometrically detectable signal is a function of the amount of the sample applied to the test field;

an optical measuring device that includes (i) a light emitter device capable of illuminating the test field with light and (ii) a light detector device capable of receiving the first photometrically detectable signal and the second photometrically detectable signal; and an electronic assembly electrically coupled to the optical measuring device, the electronic assembly being operable to:

analyze the first photometrically detectable signal received by the light detector device to determine the analyte content of the sample, wherein the determination is based on the interaction between the reagent in the test field and the analyte in the sample, and analyze the second photometrically detectable signal received by the light detector device to assess the amount of sample placed on the test element to determine whether an underdosage of the sample has occurred, wherein the assessment is based on an interaction between the control substance in the test field and a sample matrix of the sample.

10. The system of claim 9 wherein:

the analyte in the sample is glucose.

11. The system of claim 9 wherein:

the sample is blood.

* * * * *

UNITED STATES PATENT AND TRADEMARK OFFICE
CERTIFICATE OF CORRECTION

PATENT NO.         : 7,488,602 B2                                              Page 1 of 1
APPLICATION NO. : 10/686970
DATED              : February 10, 2009
INVENTOR(S)        : Pachl et al.

It is certified that error appears in the above-identified patent and that said Letters Patent is hereby corrected as shown below:

In Column 13, line 4, please delete "mafrix" and insert -- matrix -- therefor.

Signed and Sealed this

Thirty-first Day of March, 2009

JOHN DOLL
*Acting Director of the United States Patent and Trademark Office*